United States Patent
Pierce et al.

(10) Patent No.: US 10,420,633 B2
(45) Date of Patent: Sep. 24, 2019

(54) TEETH CLEANING DEVICE

(71) Applicant: COLGATE-PALMOLIVE COMPANY, New York, NY (US)

(72) Inventors: Robert Pierce, Basking Ridge, NJ (US); Nagarajan Jayaraman, New York, NY (US); Igor Kachko, Boston, MA (US); Mark Bakhrakh, Boston, MA (US); Stanislav Kolchanov, Boston, MA (US); Pavel Karavaev; Rostislav Khorenyan, Boston, MA (US); Irina Sigalovsky, Boston, MA (US); Semyon Kogan, Boston, MA (US)

(73) Assignee: Colgate-Palmolive Company, New York, NY (US)

( * ) Notice: Subject to any disclaimer, the term of this patent is extended or adjusted under 35 U.S.C. 154(b) by 315 days.

(21) Appl. No.: 15/291,760

(22) Filed: Oct. 12, 2016

(65) Prior Publication Data

US 2018/0098832 A1   Apr. 12, 2018

(51) Int. Cl.
*A61C 17/22* (2006.01)
*A61C 17/34* (2006.01)
*A46B 9/00* (2006.01)

(52) U.S. Cl.
CPC .......... *A61C 17/228* (2013.01); *A46B 9/005* (2013.01); *A61C 17/221* (2013.01); *A61C 17/222* (2013.01); *A61C 17/224* (2013.01); *A61C 17/349* (2013.01)

(58) Field of Classification Search
CPC ... A61C 17/221; A61C 17/222; A61C 17/228; A61C 17/349
See application file for complete search history.

(56) References Cited

U.S. PATENT DOCUMENTS

| | | |
|---|---|---|
| 1,894,509 A | 1/1933 | Booth |
| 2,935,755 A | 5/1960 | Ramon et al. |
| 3,504,692 A | 4/1970 | Goldstein |
| 3,630,294 A | 12/1971 | Bouyoucos et al. |
| 3,874,084 A | 4/1975 | Cole |
| 4,011,616 A | 3/1977 | Kennedy |

(Continued)

FOREIGN PATENT DOCUMENTS

| | | |
|---|---|---|
| CN | 102309133 | 1/2012 |
| WO | 2010/028383 | 3/2010 |
| WO | 2015/101897 | 7/2015 |

OTHER PUBLICATIONS

International Search Report and Written Opinion of the International Searching Authority in International Application No. PCT/US2017/055372, dated Jan. 5, 2018.

*Primary Examiner* — Randall E Chin

(57) ABSTRACT

In one embodiment, the invention may be a teeth cleaning device including: a first support structure comprising a first dentature channel configured to receive at least a first portion of a dentature of a user; a plurality of teeth cleaning pads located within the first dentature channel; a plurality of air bladders operably coupled to the teeth cleaning pads; an air-flow subsystem operably coupled to the air bladders; and a control unit operably coupled to the air-flow subsystem, the control unit configured to: (1) pressurize the air bladders with external air in a pressurization mode; and (2) transfer air between select ones of the air bladders in a cleaning mode.

15 Claims, 6 Drawing Sheets

(56) References Cited

U.S. PATENT DOCUMENTS

| | | |
|---|---|---|
| 4,224,710 A | 9/1980 | Solow |
| 4,346,492 A | 8/1982 | Solow |
| 4,538,315 A * | 9/1985 | Barth .................... A46B 13/08 15/22.1 |
| 4,795,347 A | 1/1989 | Maurer |
| 5,072,471 A | 12/1991 | Isler |
| 5,177,827 A | 1/1993 | Ellison |
| 5,184,368 A | 2/1993 | Holland |
| 5,259,083 A | 11/1993 | Stansbury |
| 5,337,435 A | 8/1994 | Krasner et al. |
| 5,497,526 A | 3/1996 | Klinkhammer |
| 5,524,319 A | 6/1996 | Avidor |
| 5,615,443 A | 4/1997 | Lai |
| 5,669,097 A | 9/1997 | Klinkhammer |
| 6,353,956 B1 | 3/2002 | Berge |
| 7,036,179 B1 | 5/2006 | Weihrauch |
| 7,082,638 B2 | 8/2006 | Koh |
| 7,334,283 B2 | 2/2008 | Kunita et al. |
| 7,600,288 B1 | 10/2009 | Givonetti |
| 7,743,452 B1 | 6/2010 | Tcholakov |
| 7,832,043 B1 | 11/2010 | Feldman |
| 8,448,282 B2 * | 5/2013 | Stapelbroek ............. A61C 7/08 15/167.2 |
| 8,359,692 B2 | 6/2013 | Brewer |
| 8,793,830 B2 | 8/2014 | Stapelbroek et al. |
| 8,990,992 B2 | 3/2015 | Stapelbroek et al. |
| 9,277,980 B2 | 3/2016 | Leveling et al. |
| 9,526,597 B2 * | 12/2016 | Steur .................... A61C 17/222 |
| 9,750,334 B2 * | 9/2017 | Kirchhofer .............. A46B 1/00 |
| 2004/0074035 A1 | 4/2004 | Huang |
| 2008/0216257 A1 | 9/2008 | Ahadpour et al. |
| 2009/0044360 A1 | 2/2009 | Davidson et al. |
| 2009/0229062 A1 | 9/2009 | Filby |
| 2010/0062397 A1 | 3/2010 | Brewer |
| 2011/0113576 A1 | 5/2011 | Yankell |
| 2013/0067665 A1 | 3/2013 | Sowinski |
| 2013/0081217 A1 | 4/2013 | Jeong |
| 2013/0089836 A1 | 4/2013 | Stapelbroek et al. |
| 2014/0373290 A1 | 12/2014 | Leveling et al. |
| 2015/0072306 A1 | 3/2015 | Barnard et al. |

* cited by examiner

TEETH CLEANING DEVICE

BACKGROUND

The present invention relates to teeth cleaning devices, particularly teeth cleaning devices which enable substantially all teeth surfaces to be cleaned simultaneously.

A type of teeth cleaning device that performs teeth brushing (plaque removal) by cleaning substantially all teeth surfaces exposed within the user's mouth simultaneously is known. Such devices may be commonly referred to as whole mouth toothbrushes. Some whole mouth toothbrushes seek to replicate the up and down motion of the Bass Method for cleaning teeth, which is widely recognized as one of the most efficient methods for removing plaque, tartar, and the like from teeth surfaces. However, although the Bass Method for cleaning teeth is one of the most recommended methods for using a manual toothbrush, it is not necessarily the most efficient method for whole mouth toothbrushes. Thus, a need exists for a teeth cleaning device that can improve the efficiency of whole mouth toothbrushes in the removal of plaque, tartar, and the like.

BRIEF SUMMARY

The present invention may be directed, in one aspect, to a teeth cleaning device including: a first support structure comprising a first dentature channel configured to receive at least a first portion of a dentature of a user; a plurality of teeth cleaning pads located within the first dentature channel; a plurality of air bladders operably coupled to the teeth cleaning pads; an air-flow subsystem operably coupled to the air bladders; and a control unit operably coupled to the air-flow subsystem, the control unit configured to: (1) pressurize the air bladders with external air in a pressurization mode; and (2) transfer air back-and-forth between select ones of the air bladders in a cleaning mode.

In another aspect, the invention may be directed to a teeth cleaning device including: a first support structure comprising a first dentature channel configured to receive at least a first portion of a dentature of a user, the first dentature channel defined by a first channel floor, a first facial wall, and a first glossal wall; a plurality of teeth cleaning pads, the teeth cleaning pads comprising: a first facial teeth cleaning pad coupled to the first facial wall; and a first glossal teeth cleaning pad coupled to the first glossal wall so as to oppose the first facial teeth cleaning pad, the first facial teeth cleaning pad and the first glossal teeth cleaning pad being oriented such that an acute angle is formed therebetween; a plurality of air bladders operably coupled to the teeth cleaning pads; and an air-flow subsystem operably coupled to the air bladders.

In another aspect, the invention may be a teeth cleaning device including: a first support structure comprising a first dentature channel configured to receive upper teeth of a dentature of a user; a second support structure comprising a second dentature channel configured to receive lower teeth of the dentature of the user; a plurality of teeth cleaning pads comprising a first set of teeth cleaning pads located within the first dentature channel and a second set of teeth cleaning pads located within the second dentature channel; a plurality of air bladders comprising a first set of air bladders operably coupled to the first set of teeth cleaning pads and a second set of air bladders operably coupled to the second set of teeth cleaning pads; an air-flow subsystem operably coupled to the air bladders; and a control unit operably coupled to the air-flow subsystem, the control unit configured to: (1) operate the air-flow subsystem to produce a first cleaning motion in a first direction with respect to the dentature of the user; (2) operate the air-flow subsystem to produce a second cleaning motion in a second direction with respect to the dentature of the user; and (3) operate the air-flow subsystem to produce a third cleaning motion in a third direction with respect to the dentature of the user, wherein the first, second, and third directions are different from one another.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
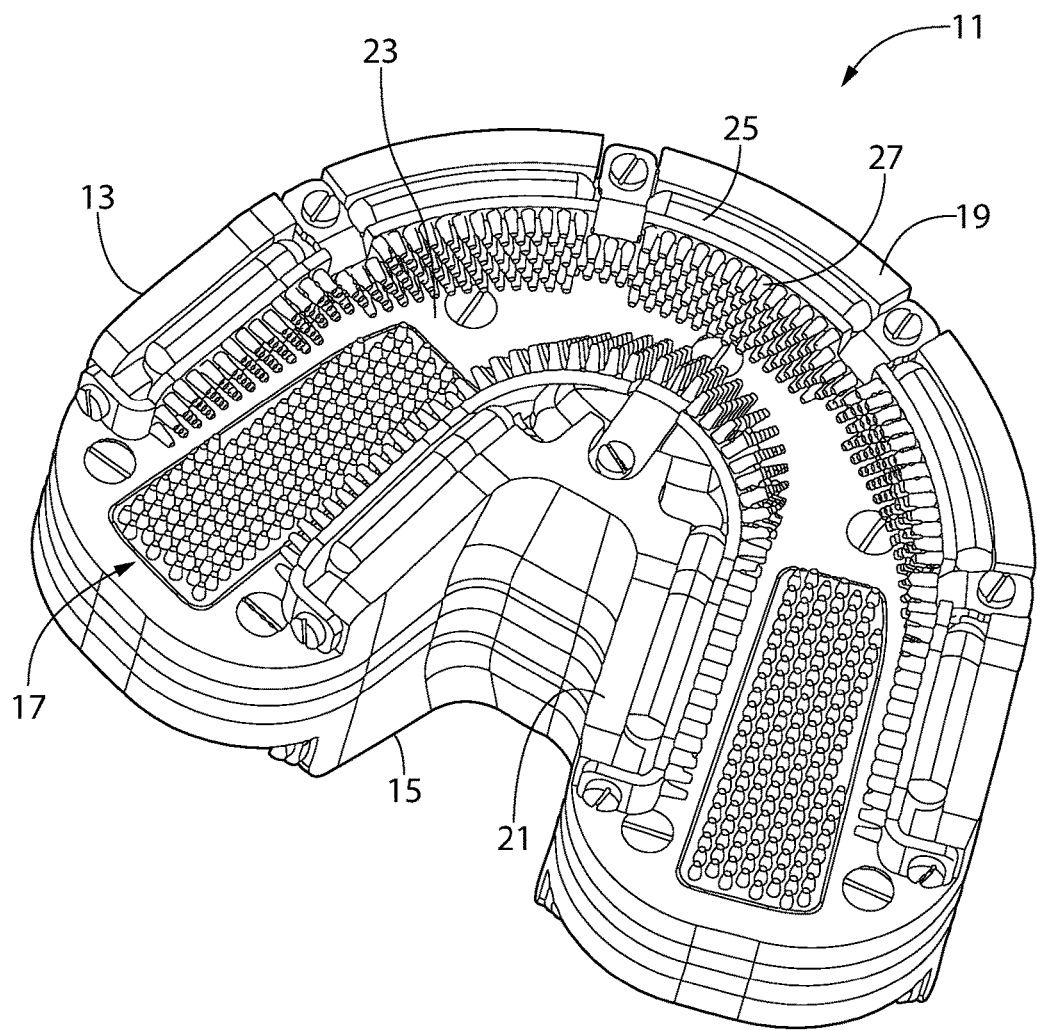
FIG. 1 is a perspective view of the support structure of a teeth cleaning device in accordance with a first embodiment.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Turning in detail to the drawings, FIG. 1 illustrates the teeth support structure of a teeth cleaning device 11 (also referred to herein as an oral care implement or a powered toothbrush in some embodiments) which includes a first support structure 13 and a second support structure 15. In this exemplary embodiment, the first support structure 13 and the second support structure 15 are configured identically. Thus, in the following description, the details concerning the first support structure 13 apply equally to the second support structure 15. In certain other embodiments, the first support structure 13 and the second support structure 15 may have configurations that vary from each other, such that one of the support structures is specifically configured for cleaning the upper teeth, and the other of the support structures is specifically configured for cleaning the lower teeth. As will become apparent from the description below, the first support structure 13 and the second support structure 15 may vary with respect to one or more of the number and placement of air bladders, the number and placement of teeth cleaning pads, the orientation of cleaning pads with respect to one another, among other types of potential variances.

In addition, while the exemplary embodiment is shown to have both first and second teeth support structures 13, 15, it is to be understood that certain embodiments of the teeth cleaning device 11 may include only one of the first or second teeth support structures 13, 15. In such embodiments, a single teeth support structure may be used first on the upper or lower teeth of a user, and then flipped around to be used on the other of the upper or lower teeth of the user.

Figure 2:
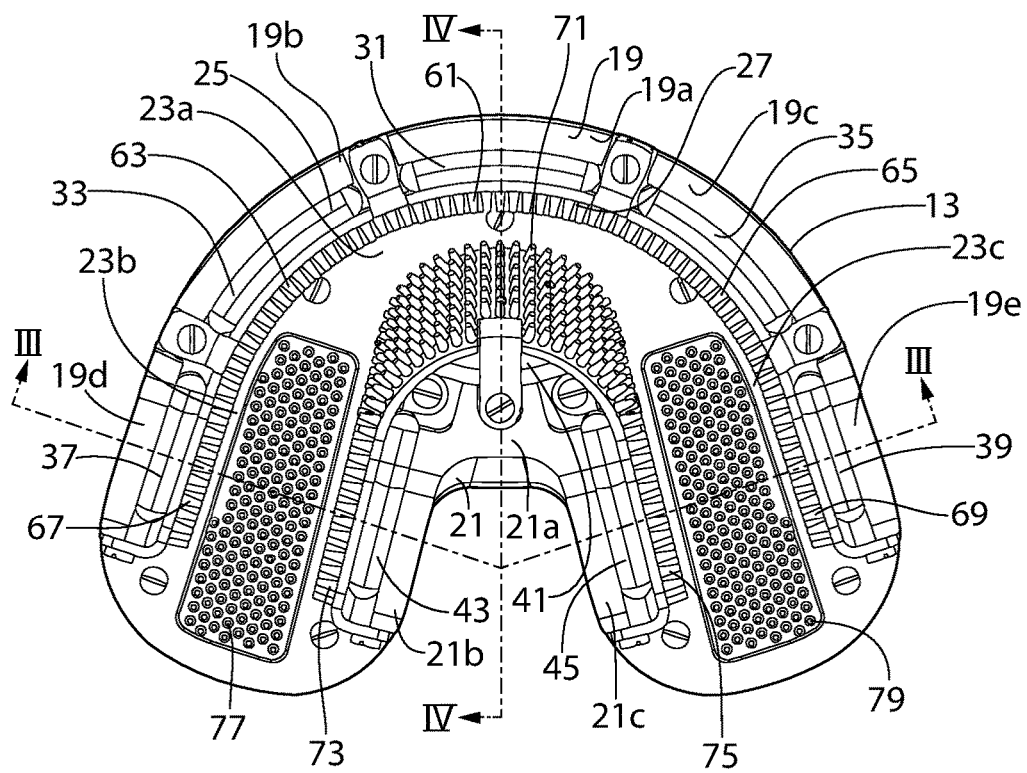
FIG. 2 is a top elevation view of the support structure of FIG. 1.
Figure 3:
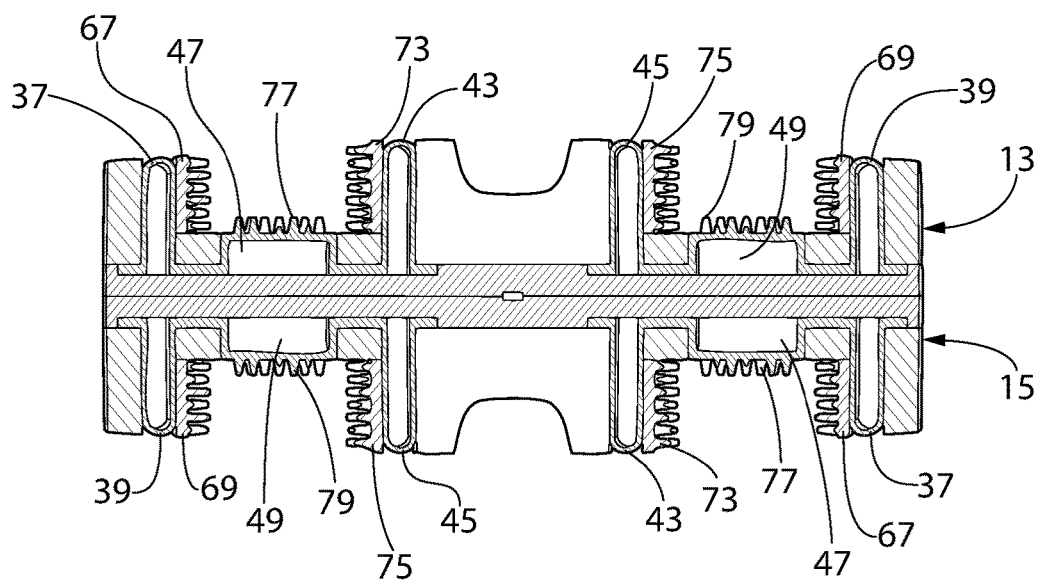
FIG. 3 is a cross sectional view of the support structure along the line III-II of FIG. 1.

Returning to FIG. 1, the first support structure 13 includes a dentature channel 17 which is shaped so that at least a portion of a user's dentature, namely at least a portion of the user's upper or lower teeth, may be received into the dentature channel 17. The dentature channel 17 is defined by a facial wall 19, a glossal wall 21, and a channel floor 23. In certain embodiments, the first support structure 13 may be formed from a material that is suitable for use within a user's mouth, such as, for example, polyetheretherketone. As seen in FIGS. 1-3, air bladders 25 are positioned adjacent each of the facial wall 19, the glossal wall 21, and the channel floor 23, and teeth cleaning pads 27 are coupled to the air bladders 25. The air bladders 25 may be secured to the first support structure 13 within the dentature channel 17 by any appropriate means, such as glue, tape, fasteners, brackets, and the like. The teeth cleaning pads 27 may be affixed to the air bladders 25 by any appropriate means, such as glue or tape. In certain embodiments, the teeth cleaning pads 27 may be used to secure the air bladders 25 in position adjacent any one or more of the facial wall 19, the glossal wall 21, and/or the channel floor 23. In certain embodiments, the teeth cleaning pads 27 may be integrally formed with the air bladders 25.

In the exemplary embodiment, the air bladders 25 may be formed of one of an elastic material such as a silicon rubber or a polyurethane. The material from which the air bladders 25 are formed may have a Shore hardness between and including 15-30 A. And in the exemplary embodiment, the teeth cleaning pads 27 may be formed of a polyurethane. The material from which the teeth cleaning pads 27 are formed may have a Shore hardness between and including 30-40 A. Of course, other materials may be used for both the air bladders 25 and the teeth cleaning pads 27, and the materials used may have a hardness outside of the stated ranges.

As shown in FIG. 2, the facial wall 19 of the first support structure 13 may include a first facial wall portion 19a, a second facial wall portion 19b, a third facial wall portion 19c, a fourth facial wall portion 19d, and a fifth facial wall portion 19e. When the first support structure 13 is inserted into the mouth of a user, with the teeth of the user positioned within the dentature channel 17, the first, second, and third facial wall portions 19a-c are positioned facing the facial surfaces of the incisor and cuspid teeth, and the fourth and fifth facial wall portions 19d-e are positioned facing the facial surfaces of the premolar and molar teeth. In certain embodiments any two or more of the facial wall portions 19a-e may be integrally formed. For example, the entire facial wall 19 may be integrally formed, so that there is no visible distinction in the facial wall 19 between the facial wall portions 19a-e. In such embodiments, the positioning of the air bladders 25 along the facial wall 19 may serve to distinguish between the different facial wall portions 19a-e. In certain embodiments, the second and third facial wall portions 19b-c may be integrated with the first facial wall portion 19a. In still other embodiments, the second and fourth facial wall portions 19b, 19d may be integrated, and the third and fifth facial wall portions 19c, 19e may be integrated. The respective sizes and positions of the facial wall portions 19a-e may vary to accommodate the difference in tooth and mouth sizes of different users and is not intended to be limiting of the invention.

The glossal wall 21 of the first support structure 13 may include a first glossal wall portion 21a, a second glossal wall portion 21b, and a third glossal wall portion 21c. When the first support structure 13 is inserted into the mouth of a user, with the teeth of the user positioned within the dentature channel 17, the first glossal wall portion 21a is positioned facing the glossal surfaces of the incisor and cuspid teeth, and the second and third wall portions 21b-c are positioned facing the glossal surfaces of the premolar and molar teeth. In certain embodiments, any two or more of the glossal wall portions 21a-c may be integrally formed. For example, the entire glossal wall 21 may be integrally formed, so that there is no visible distinction in the glossal wall 21 between the glossal wall portions 21a-c. In such embodiments, the positioning of the air bladders 25 along the glossal wall 21 may serve to distinguish between the different glossal wall portions 21a-c. The respective sizes and positions of the glossal wall portions 21a-c may vary to accommodate the difference in tooth and mouth sizes of different users and is not intended to be limiting of the invention.

The channel floor 23 of the first support structure 13 may be viewed as including a first floor portion 23a, a second floor portion 23b, and a third floor portion 23c. When the first support structure 13 is inserted into the mouth of a user, with the teeth of the user positioned within the dentature channel 17, the first floor portion 23a is positioned facing the biting surfaces of the incisor and cuspid teeth, and the second and third floor portions 23b-c are positioned facing the biting surfaces of the premolar and molar teeth. In certain embodiments any two or more of the floor portions 23a-c may be integrally formed. For example, the entire channel floor 23 may be integrally formed, so that there is no visible distinction in the channel floor 23 between the floor portions 23a-c. In such embodiments, the positioning of the air bladders 25 along the channel floor 23 may serve to distinguish between the different floor portions 23a-c. The respective sizes and positions of the floor portions 23a-c may vary to accommodate the difference in tooth and mouth sizes of different users and is not intended to be limiting of the invention.

The exemplary embodiment includes, along the facial wall 19, a first facial air bladder 31 adjacent the first facial wall portion 19a, a second facial air bladder 33 adjacent the second facial wall portion 19b, a third facial air bladder 35 adjacent the third facial wall portion 19c, a fourth facial air bladder 37 adjacent the fourth facial wall portion 19d, and a fifth facial air bladder 39 adjacent the fifth facial wall portion 19e. When the first support structure 13 is inserted into the mouth of a user, with the teeth of the user positioned within the dentature channel 17, the first, second, and third facial air bladders 31, 33, 35 are positioned between the facial surfaces of the incisor and cuspid teeth and the respective first, second, and third facial wall portions 19a-c, and the fourth and fifth air bladders 37, 39 are positioned between the facial surfaces of the premolar and molar teeth and the respective fourth and fifth facial wall portions 19d-e. In certain embodiments, additional air bladders 25 may be included adjacent to the facial wall 19. In still other embodiments, such as the embodiment shown in FIG. 8, fewer air bladders 25 may be included adjacent to the facial wall 19.

Along the glossal wall 21, the exemplary embodiment includes a first glossal air bladder 41, a second glossal air bladder 43, and a third glossal air bladder 45. When the first support structure 13 is inserted into the mouth of a user, with the teeth of the user positioned within the dentature channel 17, the first glossal air bladder 41 is positioned between the glossal surfaces of the incisor and cuspid teeth and the first glossal wall portion 21a, and the second and third air bladders 43, 45 are positioned between the glossal surfaces of the premolar and molar teeth and the respective second and third glossal wall portions 21b-c. In certain embodiments, more or fewer air bladders 25 may be included adjacent to the glossal wall 21.

Along the channel floor 23, the exemplary embodiment includes a first floor air bladder 47 and a second floor air bladder 49. When the first support structure 13 is inserted into the mouth of a user, with the teeth of the user positioned within the dentature channel 17, the first and second floor air bladders 47, 49 are positioned between the biting surfaces of the premolar and molar teeth and the respective second and third floor portions 23b-c. In certain embodiments, additional air bladders 25 may be included adjacent to the channel floor 23. For example, an air bladder 25 may be included along the first floor portion 23a. As another example, the second and third floor portions 23b-c may have two or more air bladders adjacent thereto.

The teeth cleaning pads 27 along the facial wall 19 extend continuously around the facial wall 19 and are coupled to the air bladders 25 adjacent the facial wall 19. Similarly, teeth cleaning pads 27 along the glossal wall 21 extend continuously around the glossal wall 21 and are coupled to the air bladders 25 adjacent the glossal wall 21. In the exemplary embodiment, the teeth cleaning pads 27 extend between any gaps that may be formed between the air bladders 25. In certain embodiments, gaps may be left between teeth cleaning pads 27, with those gaps closing upon pressurization of the air bladders 25. Two floor teeth cleaning pads 57 are positioned on the channel floor 23. In the exemplary embodiment, the floor cleaning pads 57 are contiguous. However, in certain other embodiments, the floor cleaning pads 57 may extend continuously along the channel floor 23.

In the exemplary embodiment, the teeth cleaning pads 27 along the glossal wall 19 include a first facial teeth cleaning pad 61 coupled to the first facial air bladder 31, a second facial teeth cleaning pad 63 coupled to the second facial air bladder 33, a third facial teeth cleaning pad 65 coupled to the third facial air bladder 35, a fourth facial teeth cleaning pad 67 coupled to the fourth facial air bladder 37, and a fifth facial teeth cleaning pad 69 coupled to the fifth facial air 39. When the first support structure 13 is inserted into the mouth of a user, with the teeth of the user positioned within the dentature channel 17, the first, second, and third facial teeth cleaning pads 61, 63, 65 are positioned to engage the facial surfaces of the incisor and cuspid teeth when the respectively coupled first, second, and third facial air bladders 31, 33, 35 are pressurized, and the fourth and fifth facial teeth cleaning pads 67, 69 are positioned to engage the facial surfaces of the premolar and molar teeth when the fourth and fifth facial air bladders 37, 39 are pressurized. In certain embodiments, any two or more of the facial teeth cleaning pads 61, 63, 65 may be integrally formed.

The teeth cleaning pads 27 along the glossal wall 21 include a first glossal teeth cleaning pad 71 coupled to the first glossal air bladder 41, a second glossal teeth cleaning pad 73 coupled to the second glossal air bladder 43, a third glossal teeth cleaning pad 75 coupled to the third glossal air bladder 45. When the first support structure 13 is inserted into the mouth of a user, with the teeth of the user positioned within the dentature channel 17, the first glossal teeth cleaning pad 71 is positioned to engage the glossal surfaces of the incisor and cuspid teeth when the coupled first glossal air bladder 41 is pressurized, and the second and third glossal teeth cleaning pads 73, 75 are positioned to engage the glossal surfaces of the premolar and molar teeth when the second and third glossal air bladders 43, 45 are pressurized. In certain embodiments, any two or more of the facial teeth cleaning pads 61, 63, 65 may be integrally formed.

Turning to FIG. 3, the teeth cleaning pads 27 along the channel floor 23 include a first floor teeth cleaning pad 77 coupled to the first floor air bladder 47 and a second floor teeth cleaning pad 79 coupled to the second floor air bladder 49. When the first support structure 13 is inserted into the mouth of a user, with the teeth of the user positioned within the dentature channel 17, the first and second floor teeth cleaning pads 77, 79 are positioned to engage the biting surfaces of the premolar and molar teeth when the first and second floor air bladders 47, 49 are pressurized. In the exemplary embodiment, each air bladder 25 has one of the teeth cleaning pads 27 coupled thereto. In certain other embodiments, each air bladder 25 may have more than one of the teeth cleaning pads 27 coupled thereto.

Figure 4:
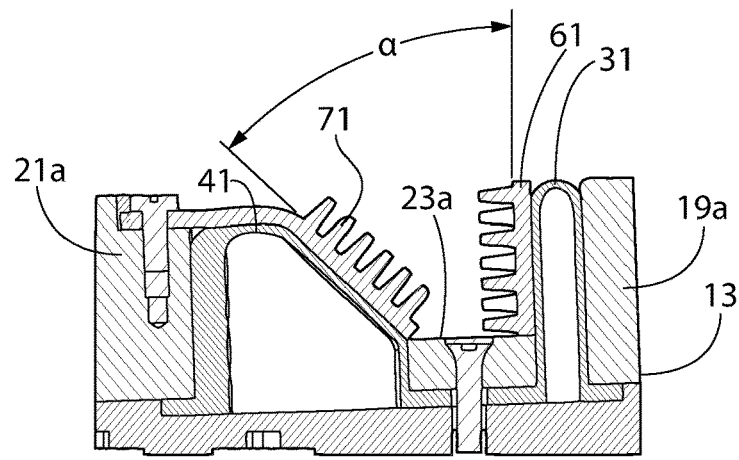
FIG. 4 is a cross sectional view of the support structure along the line IV-IV of FIG. 1.
Figure 5:
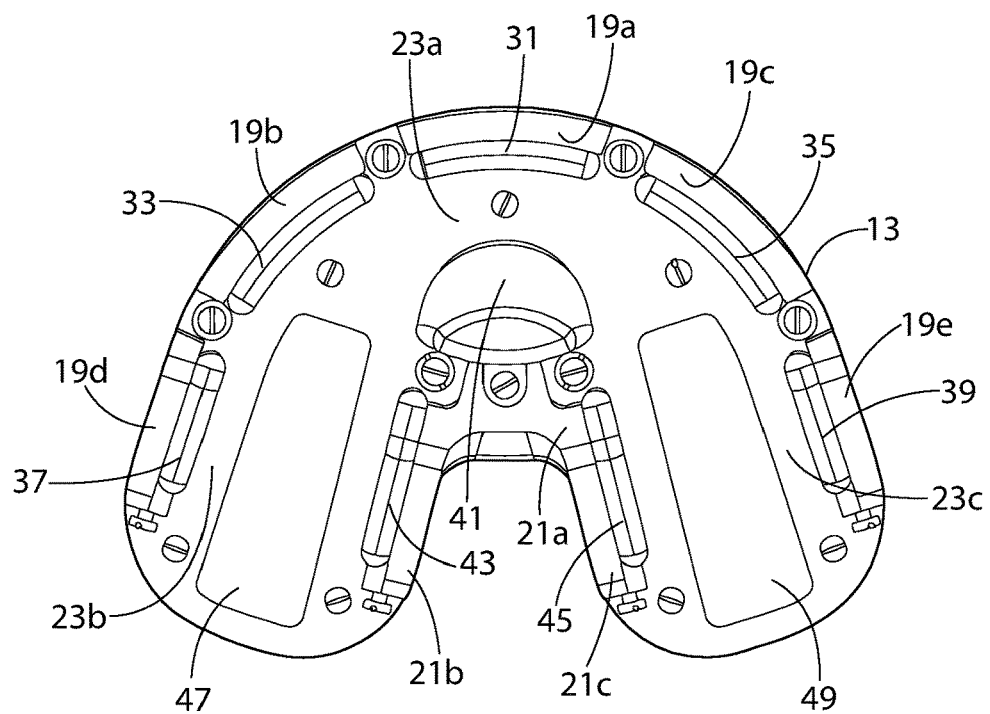
FIG. 5 is a top elevation view of the support structure of FIG. 1 without the teeth cleaning pads.

As shown in FIGS. 4 and 5, in the plane of the drawing, which is in a plane bisecting the facial and glossal walls 19, 21, the first facial teeth cleaning pad 61 is positioned at a first angle with respect to the first floor portion 23a of the first support structure 13 and the first glossal teeth cleaning pad 71 is positioned at a second angle with respect to the first floor portion 23a of the first support structure 13, with the first angle being different from the second angle. With such orientations, an acute angle, α, is formed between the first facial teeth cleaning pad 61 and the first glossal teeth cleaning pad 71. In the exemplary embodiment, the first facial teeth cleaning pad 61 is perpendicular to the first floor portion 23a, and the first glossal teeth cleaning pad 71 is at an oblique angle with respect to the first floor portion 23a. The respective angles of the first facial teeth cleaning pad 61 and the first glossal teeth cleaning pad 71 aids in more efficiently cleaning the facial, glossal, and biting surfaces of incisors and cuspids. Particularly, having the first glossal teeth cleaning pad 71 at an oblique angle to the first floor portion 23a aids in cleaning both the glossal and biting surfaces of incisors and cuspids without requiring the addition of a teeth cleaning pad positioned along the first floor portion 23a. It should be noted that in certain embodiments, the first channel floor (or at least a portion thereof . . . such as the first floor portion 23a) may simply be in the form of a line or apex formed by the convergence of the first facial wall and the first glossal wall (or portions thereof).

The teeth cleaning pads other than the first glossal teeth cleaning pad 71 may be positioned at a third angle, and this third angle may be different from both the first and second angles, or it may be the same as the first angle. In certain embodiments, the teeth cleaning pads 27 other than the first glossal teeth cleaning pad 71 are positioned perpendicular to the channel floor 23. In certain other embodiments, the angles of all teeth cleaning pads 27 may vary along the facial and glossal walls 19, 21, and such variation in angle may provide improved cleaning of all exposed teeth surfaces through better engagement of the teeth cleaning pads 27, when the air bladders 25 are pressurized, with exposed teeth surfaces. The invention, however, is not to be limited by the respective angles of the various teeth cleaning pads 27 unless otherwise so limited in the claims. In certain embodiments, the teeth cleaning pads 27 may all be positioned at the same angle with respect to the channel floor 23.

In furtherance of improving the cleaning of exposed teeth surfaces, the channel floor 23 may vary in width. In the exemplified embodiment, the first floor portion 23a of the first support structure 11 has a first width and the second and third floor portions 23b-c of the first support structure 11 have a second width, with the first width being less than the second width. The first width may be such that the first facial teeth cleaning pad 61 adjacent the first facial wall portion 19a and the first glossal teeth cleaning pad 71 adjacent the first glossal wall portion 21a are closer together than the teeth cleaning pads 27 opposite each other elsewhere on the facial and glossal walls 19, 21. The narrowness of the first width, as compared to the second width, is an additional factor, along with the respective angles of the first facial teeth cleaning pad 61 and the first glossal teeth cleaning pad 71, in the exclusion of teeth cleaning pads 27 along the first floor portion 23a. In certain embodiments, the first width of the first floor portion 23a may be reduced to a line of intersection between the first facial wall 19a and the first glossal wall 21a. The combination of the respective angles of the first facial teeth cleaning pad 61 and the first glossal teeth cleaning pad 71 and the first width of the first floor portion 23a may result, in certain embodiments, in the first facial teeth cleaning pad 61 and the first glossal teeth cleaning pad 71 coming into contact with each other, or being nearly in contact with each other, adjacent to the first floor portion 23a before pressurization of the respective air bladders 31, 41. The differences in widths helps conform the dentature channel 17 better to the widths of the teeth being cleaned. Generally speaking, incisor and cuspid teeth have a narrower width than pre-molar and molar teeth. Thus, the dentature channel 17 is constructed so that the part of the channel intended to receive incisors and cuspids, namely the first floor portion 23a, has a narrower width than the part of the part of the channel intended to receive pre-molars and molars, namely the second and third floor portions 23b-c. Of course, the invention is not to be so limited, and in certain embodiments, the entire channel floor 23 may have a constant width.

Although not shown in the figures depicting the first embodiment of the teeth cleaning device 11, the first (and second) support structure 13 includes air supply ducts extending from an input duct to each of the air bladders 25. The air supply ducts are included for supplying pressurized air to all air bladders. The air supply ducts are shown schematically in FIG. 9, which depicts a second embodiment of the teeth cleaning device.

As will become apparent from the ensuing description, during use the teeth cleaning pads 27 along the facial wall 19 engage and clean the facial surface of a user's teeth, the teeth cleaning pads 27 along the glossal wall 21 engage and clean the glossal surface of a user's teeth, and the teeth cleaning pads 27 along the channel floor 23 engage and clean the biting surfaces of a user's pre-molars and molars. Each teeth cleaning pad 27 is coupled to an air bladder, and each air bladder, when pressurized, expands to displace the teeth cleaning pads 27 into the dentature channel 17 to engage the respective teeth surfaces.

Figure 6A:
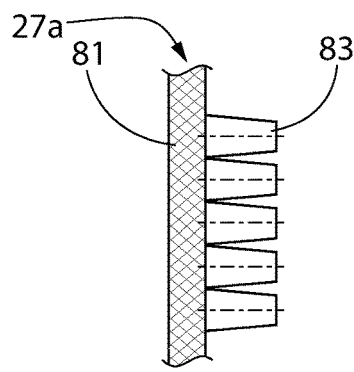
FIG. 6A is a partial side cross-sectional view of a first embodiment of a teeth cleaning pad.
Figure 6B:
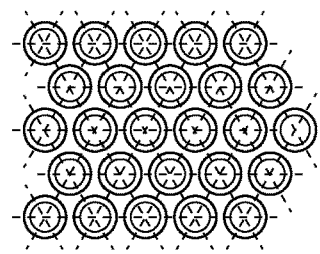
FIG. 6B is a partial top planar view of the first embodiment of the teeth cleaning pad.
Figure 7A:
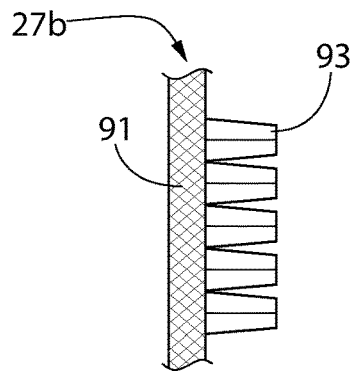
FIG. 7A is a partial side cross-sectional view of a second embodiment of a teeth cleaning pad.
Figure 7B:
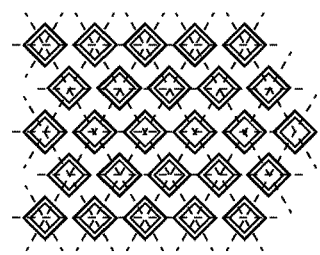
FIG. 7B is a partial top planar view of the second embodiment of the teeth cleaning pad.

FIGS. 6A-B and 7A-B show two different exemplary embodiments for the teeth cleaning pads 27a, 27b. Referring to the teeth cleaning pad 27a shown in FIGS. 6A-B, the teeth cleaning pad 27 a includes a substrate layer 81 and a plurality of teeth cleaning elements 83. In certain embodiments, the substrate layer 81 may be one surface of an air bladder 25. In certain other embodiments, the substrate layer 81 is affixed to a surface of an air bladder 25. The teeth cleaning elements 83 may serve at least two functions during use of the cleaning device 11. First, the teeth cleaning elements 83 may serve to support the teeth cleaning device 11 within the user's mouth during use. To help fulfill this first purpose, the teeth cleaning elements 83 are supported by a sufficiently a large surface area (i.e., the air bladders 25) and they are constructed to have a suitable rigidity when the air bladders 25 are pressurized and press the teeth cleaning elements 83 against the exposed teeth surfaces. The teeth cleaning elements 83, in the exemplary embodiment, therefore, are formed from an appropriate material, such as is disclosed above, and they are formed to have a density to ensure sufficient engagement with exposed teeth surfaces when the air bladders are pressurized. The second function of the teeth cleaning elements 83 is to provide the desired cleaning of exposed teeth surfaces. To serve both these functions, the teeth cleaning elements 83 of FIGS. 6A-B are formed as truncated cones 83. The truncated cone teeth cleaning elements 83 have a large base end coupled to the substrate layer 81, the larger base helping to provide the desired support and rigidity, and a smaller tip end, which engages exposed teeth surfaces to help provide the desired support and to provide the desired cleaning. The truncated cones 83 are positioned on the substrate 81 to form a hexagonal grid, thus providing the desired density. FIGS. 7A-B show a second embodiment for the teeth cleaning pads 27. In this embodiment, the teeth cleaning elements 93 affixed to the substrate layer 91 are formed as truncated pyramids. Like the truncated cones, the truncated pyramid teeth cleaning elements 93 have a large base end coupled to the substrate layer 91 and a smaller tip end. Similarly, the truncate pyramid teeth cleaning elements 93 are positioned on the substrate 81 to form a hexagonal grid. In certain embodiments, the teeth cleaning elements may take other forms or shapes, such as bristles, as the invention is not to be limited by the form of the teeth cleaning elements.

Figure 8:
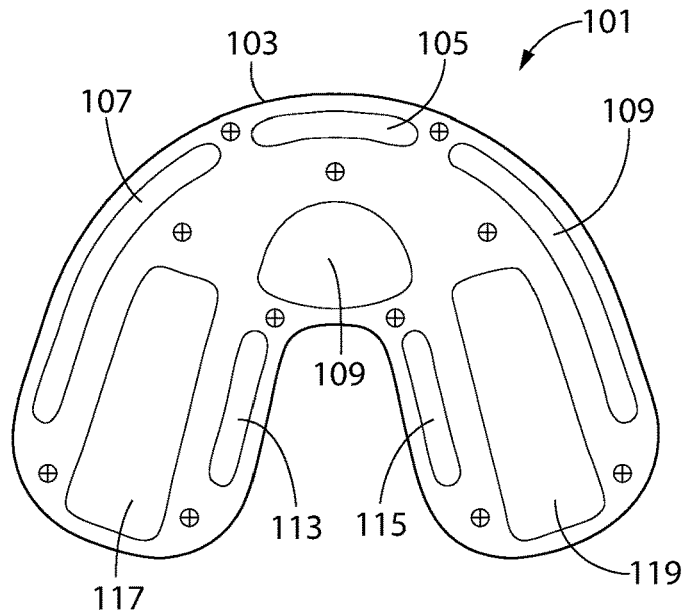
FIG. 8 is a schematic view of a top support structure of a teeth cleaning device in accordance with a second embodiment.

FIG. 8 shows a schematic view of a second embodiment of a teeth cleaning device 101 and the positions of air bladders with respect to the teeth support structure 103; the channel walls and teeth cleaning pads are omitted for purposes of clarity. The teeth cleaning device 101 is shown with two sets of air bladders 25, one set as part of a first support structure (those air bladders with reference numbers ending with 'a') and the other set as part of a second support structure (those air bladders with reference numbers ending with 'b'). It is to be understood that, as with the first embodiment described above, each air bladder of this second embodiment is positioned adjacent a respective wall portion, which defines the dentature channel, and is coupled to a respective teeth cleaning pad. The teeth cleaning device 101 includes a first facial air bladder 105, a second facial air bladder 107, a third facial air bladder 109, a first glossal air bladder 111, a second glossal air bladder 113, a third glossal air bladder 115, a first floor air bladder 117, and a second floor air bladder 119. These various air bladders are positioned on the teeth support structure 103 in a manner as described above to effectuate cleaning of facial, glossal, and biting surfaces of a user's teeth during use.

Figure 9:
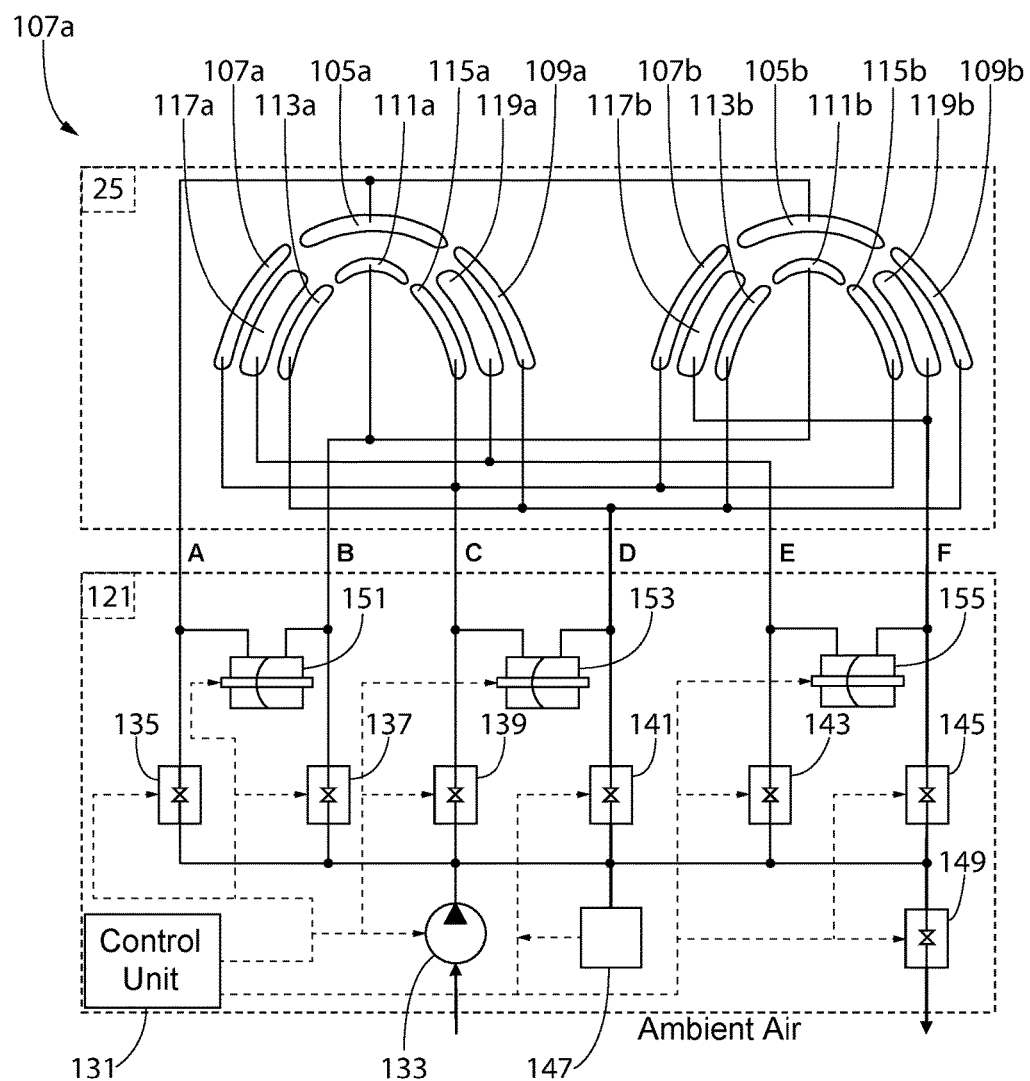
FIG. 9 is a schematic view of the air and control pathways of a teeth cleaning device in accordance with the second embodiment.

The teeth cleaning device 101 is shown schematically in FIG. 9, and includes an air-flow subsystem 121 for pressurizing the air bladders. The air-flow subsystem 121 is operably coupled to a control unit 131, which operates the air-flow subsystem 121 for pressurizing and controlling the air pressure in the air bladders. The control unit 131 is configured to operate the air-flow subsystem 121 to (1) pressurize the air bladders 25 with external air in a pressurization mode; and (2) transfer air back-and-forth between select ones of the air bladders 25 in a cleaning mode. In the cleaning mode, part of the air-flow subsystem 121 and the air bladders 25 form a closed circuit, such that air is neither received from nor discharged from the closed circuit to atmosphere during the cleaning mode. In one such embodiment, in cleaning mode, a fixed amount (i.e., a fixed volume or a fixed mass) of air is contained within the air-flow subsystem for distribution between selected air bladders in an alternating and repetitive manner, thereby achieving a brushing motion (described in greater detail below). The air-flow subsystem 121 may have any appropriate configuration of components (such as pumps, valves, conduits, flow restrictors, etc.) for performing both the pressurization mode and the cleaning mode and, in certain embodiments, is not be limited to any specific fluid circuit arrangement. The air-flow subsystem 121 is therefore not to be limited to the specific components described herein in relation to the exemplary embodiment. The control unit 131 may be any type of programmable control unit, including those programmed through software or those which are programmed in hardware. Through control connections, the control unit 131 is operably coupled to various components of the air-flow subsystem 121, which may include the air pump 133, a plurality of valves 135-145, a pressure sensor 147, a discharge valve 149, and a plurality transfer pumps 151-155. The control unit 131 controls each of these other components using appropriate control signals, or in the case of the pressure sensor 147, receives a signal as input, and in response to that signal, may perform certain functions as described below.

The air pump 133 has an air intake to take in air from ambient atmosphere, generate pressurized air within the air supply ducts of the air-flow subsystem 121, and the pressurized air is used to pressurize the air bladders 25. Each valve 135-145 operably couples the air pump 133 to one or more of the air bladders 25. The air pump 133 directs the pressurized air through each of the valves 135-145, which remain in an open position during the pressurization process. During the pressurization process, the control unit 131 signals the discharge valve 149 to remain in the closed position. The pressure sensor 147 monitors the air pressure within the air-flow subsystem 121, and particularly within the air bladders 25, and communicates the measured air pressure as an electronic signal to the control unit 131. When the control unit 131 determines that the air pressure within the air-flow subsystem 121 is at or above a predetermined air pressure, then the control unit 131 signals the air valves 135-145 to move to the closed position and shuts off the air pump 147. The predetermined pressure may be set by ensuring that the teeth cleaning elements fully engage the exposed surfaces of teeth within a user's mouth without gaps.

In the closed position, the air valves 135-145 seal the air bladders 25 from the air pump 133 so that the air bladders 25 remain pressurized. As indicated above, when the air bladders 25 are pressurized, the teeth cleaning pad associated with each air bladder 25 is displaced into the respective dentature channel. At any time during or after the brushing process, the control unit 131 may depressurize the air bladders 25 by signaling the air valves 135-145 to move to the open position and by signaling the discharge valve 149 to move to the open position, so that the pressurized air within the air bladders 25 is released to atmosphere through the discharge valve 149.

Each valve 135-145 is coupled to a set of the air bladders 25, and each set of the air bladders 25 includes at least one air bladder 25. While in the exemplary embodiment the control unit 131 operates the valves 135-145 as a unit to pressurize and depressurize all the air bladders 25, in certain embodiments the control unit 131 may operate on or more of the valves 135-145 individually to pressurize or depressurize specific sets of the air bladders 25 independently of the other sets of the air bladders 25.

As shown in FIG. 9, the air bladders are grouped in sets as follows (as identified by the air ducts feeding into the respective sets air bladders 25):

Set A: the first facial air bladder 105*a* of the first support structure and the first facial air bladder 105*b* of the second support structure (this set is coupled to the air pump 133 through valve 135);

Set B: the first glossal air bladder 111*a* of the first support structure and the first glossal air bladder 111*b* of the second support structure (this set is coupled to the air pump 133 through valve 137);

Set C: the second facial air bladder 107*a* and the third glossal air bladder 115*a* of the first support structure and the second facial air bladder 107*b* and the third glossal air bladder 115*b* of the second support structure (this set is coupled to the air pump 133 through valve 139);

Set D: the second glossal air bladder 113*a* and the third facial air bladder 109*a* of the first support structure and the second glossal air bladder 113*b* and the third facial air bladder 109b of the second support structure (this set is coupled to the air pump 133 through valve 141);

Set E: the first and second floor air bladders 117a, 119a of the first support structure (this set is coupled to the air pump 133 through valve 143); and Set F: the first and second floor air bladders 117b, 119b of the second support structure (this set is coupled to the air pump 133 through valve 145).

As can be seen from these groupings, the facial air bladders 105a, 105b of Set A are located opposite respective dentature channels from the glossal air bladders 111a, 111b of Set B. With respect to Set C and Set D, each of the air bladders 107a-b, 115a-b of Set C is located opposite respective dentature channels from one of the air bladders 109a-b, 113a-b of Set D. Finally, each of the air bladders 117a-b and 119a-b of Set E and Set F is a located adjacent a channel floor. Other groupings of the air bladders 25 are possible and may prove to be advantageous during operation. As such, unless expressly stated in the claims, the invention is not to be limited by the groupings of the air bladders.

As shown, one of the transfer pumps 151-155 is operably coupled between two of the sets of air bladders 25. In certain embodiments, the transfer pumps 151-155 may be double-chamber membrane pumps, although other types of pumps which are capable of performing the function of the transfer pumps 151-155 as described herein may be used. The transfer pump 151 is operably coupled between Set A and Set B, the transfer pump 153 is operably coupled between Set C and Set D, and the transfer pump 155 is operably coupled between Set E and Set F. When the air bladders 25 are pressurized and the valves 135-145 are closed, the transfer pumps 151-155 may be operated by the control unit 131 to redistribute air between the sets of bladders 25 coupled thereto. The redistribution of air between the sets of bladders 25 creates a positive pressure change in one set and a negative pressure change in the other set. As described below, the redistribution of air between sets of bladders may be used to generate motion of the cleaning device 101 relative to the mouth of the user. The control unit 131 may selectively operate the transfer pumps 151-155 in any manner or sequence. For example, in certain embodiments, the transfer pumps 151-155 may be operated simultaneously; in certain other embodiments, the transfer pumps 151-155 may all be operated sequentially; and in yet other embodiments, any two or more of the transfer pumps may be operated simultaneously.

During use, when portions of the dentature of the user are placed in the first and second dentature channels the device is placed in a mouth with upper teeth positioned in the first dentature channel and with lower teeth positioned in the second dentature channel, operation of the first transfer pump 151 produces a first cleaning motion in a first direction with respect to the dentature of the user; operation of the second transfer pump 153 produces a second cleaning motion in a second direction with respect to the dentature of the user; operation of the third transfer pump 155 produces a third cleaning motion in a third direction with respect to the dentature of the user. In the exemplary embodiment, the three directions for each of the three cleaning motions are different from each other. By way of example, with the first transfer pump 151 redistributing air between the air bladders 25 of Set A and Set B, a motion for the cleaning device 101 in a first direction forward and backward relative to the user's jaws is generated. This first direction of motion generates a first cleaning motion of other air bladders 25 not in Set A or Set B against facial, glossal, and biting surfaces of pre-molar and molar teeth. With the second transfer pump 153 redistributing air between the air bladders 25 of Set C and Set D, a motion for the cleaning device 101 in a second direction left to right relative to the user's jaws is generated. This second direction of motion generates a second cleaning motion of other air bladders 25 not in Set C or Set D against facial, glossal, and biting surfaces of incisor and cuspid teeth. With the third transfer pump 155 redistributing air between the air bladders 25 of Set E and Set F, a motion for the cleaning device 101 in a third direction upward and downward relative to the user's jaws is generated. This third direction of motion generates a third cleaning motion of other air bladders 25 not in Set E or Set F against facial and glossal surfaces of all teeth. In each of these modes of operation, generating the cleaning motion reciprocates certain ones of the teeth cleaning pads 27 across one or more surfaces of the user's teeth to effectuate a more thorough cleaning.

The control unit 131 may operate the transfer pumps 151-155 at a predetermined flow rate to achieve a predetermined frequency in redistributing the air between the coupled sets of air bladders 25. In certain embodiments, the predetermined frequency may be between and including about 2 Hz to 30 Hz. Frequencies outside this range may be used in certain other embodiments. In still other embodiments, a varying frequency may be used for any one or more of the transfer pumps 151-155. The frequency at which any one or more of the transfer pumps 151-155 is operated may be dependent upon the user, based on, for example, the tolerance of the user to the motion that is generated or the amount of tartar and/or plaque the user has on their teeth. The control unit 131 may be preprogrammed with specific programs of operating the transfer pumps 151-155 to effectuate cleaning of the users teeth. Each program may include instructions to operate the transfer pumps in a particular sequence, whether simultaneously or sequentially, or some combination of both, and the instructions may designate operating frequencies, or frequency ranges or even changing through a sequence of two or more designated frequencies.

The manner in which the control unit 131 operates one or all of the transfer pumps 151-155, including the sequence in which they are operated and/or the frequency at which they are operated, is not intended to be limiting of the invention unless otherwise expressly stated in the claims.

Figure 10:
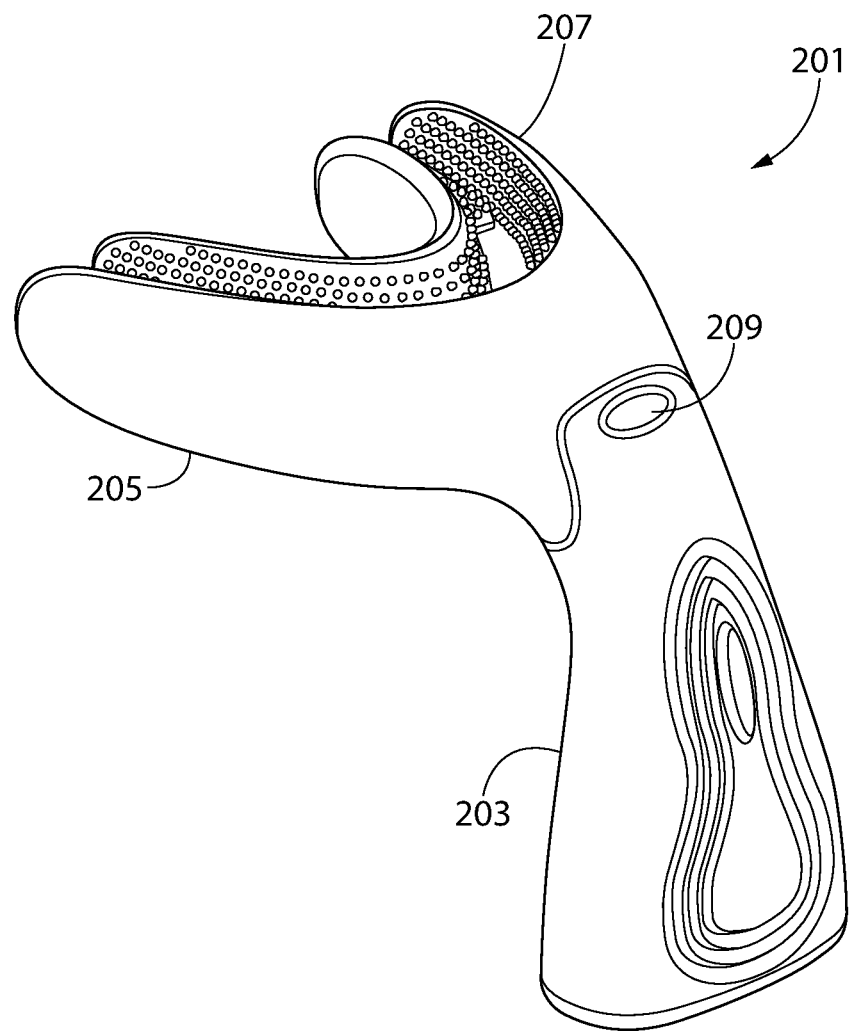
FIG. 10 is a perspective view of a teeth cleaning device in accordance with a third embodiment.

FIG. 10 illustrates an exemplary teeth cleaning device 201 which includes a handle 203 and a cleaning unit 205. The cleaning unit 205 includes first and second support structures 207, including air bladders and teeth cleaning pads, as described in connection with one or more of the embodiments above. The handle 205 is made so that it is possible to accommodate an air-flow subsystem as described above in FIG. 9, including the control unit, valves, transfer pumps, and the needed power sources (e.g., rechargeable battery) within the housing. The handle 203 includes a button 209 which is operably coupled to the control unit and/or power source so that the user may start and stop the air-flow subsystem. The handle 203 may also include a connection port (not shown) for connecting the air-flow subsystem to a power source for purposes of recharging the battery. In certain embodiments, the battery may be recharged through the use of wireless inductive charging.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A teeth cleaning device comprising:
   a first support structure comprising a first dentature channel configured to receive at least a first portion of a dentature of a user;
   a plurality of teeth cleaning pads located within the first dentature channel;
   a plurality of air bladders operably coupled to the teeth cleaning pads;
   an air-flow subsystem operably coupled to the air bladders, the air-flow subsystem comprising:
      an air pump;
      at least one valve; and
      at least one transfer pump; and
   a control unit operably coupled to the air-flow subsystem, the control unit configured to: (1) pressurize the air bladders with external air in a pressurization mode; and (2) transfer air between select ones of the air bladders in a cleaning mode;
   wherein the control unit controls pressurization of the air bladders and transfers air between the select ones of the air bladders by controlling the air pump, the at least one valve, and the at least one transfer pump.

2. The device according to claim 1, wherein each teeth cleaning pad is integrally formed with one of the air bladders.

3. The device according to claim 1, wherein the plurality of air bladders comprises a first set of air bladders and a second set of air bladders, each of the first set of air bladders and the second set of air bladders comprising at least one of the air bladders.

4. The device according to claim 3, wherein:
   the first set of the air bladders comprises a first air bladder located adjacent a facial wall of the first dentature channel; and
   the second set of the air bladders comprises a second air bladder located adjacent a glossal wall of the dentature channel so as to oppose the first air bladder.

5. The device according to claim 3, wherein:
   the first set of the air bladders comprises a first air bladder located adjacent a facial wall of the dentature channel and a second air bladder located adjacent a glossal wall of the dentature channel; and
   the second set of the air bladders comprises a third air bladder located adjacent the glossal wall of the dentature channel and a fourth air bladder located adjacent the facial wall of the dentature channel, the first air bladder opposing the third air bladder and the second air bladder opposing the fourth air bladder.

6. The device according to claim 3, further comprising a second support structure comprising a second dentature channel configured to receive at least a second portion of the dentature of the user.

7. The device according to claim 6, wherein:
   the first set of the air bladders comprises a first air bladder located adjacent a first channel floor of the first dentature channel; and
   the second set of the air bladders comprises a second air bladder located adjacent a second channel floor of the second dentature channel.

8. The device according to claim 1, wherein the at least one valve has an open position for the air pump to pressurize one or more of the air bladders and a closed position to seal the one or more of the air bladders from the air pump, wherein when one or more of the air bladders are pressurized, the teeth cleaning pads are displaced into the dentature channel.

9. The device according to claim 1, wherein the air-flow subsystem comprises a pressure release valve operably coupled to the air bladders.

10. The device according to claim 1, wherein each air bladder is formed of one of a silicon rubber or a polyurethane.

11. The device according to claim 1, wherein each air bladder has a Shore hardness between and including 15-30 A.

12. The device according to claim 1, wherein each teeth cleaning pad comprises a plurality of teeth cleaning elements.

13. The device according to claim 12, wherein the teeth cleaning elements are formed of a polyurethane material.

14. The device according to claim 12, wherein the teeth cleaning elements are formed of a material having a Shore hardness between and including 30-40 A.

15. A teeth cleaning device device comprising:
   a first support structure comprising a first dentature channel configured to receive at least a first portion of a dentature of a user;
   a plurality of teeth cleaning pads located within the first dentature channel;
   a plurality of air bladders operably coupled to the teeth cleaning pads;
   an air-flow subsystem operably coupled to the air bladders; and
   a control unit operably coupled to the air-flow subsystem, the control unit configured to: (1) pressurize the air bladders with external air in a pressurization mode; and (2) transfer air between select ones of the air bladders in a cleaning mode;
   wherein the plurality of air bladders comprises a first set of air bladders, a second set of air bladders, a third set of air bladders, a fourth set of air bladders, a fifth set of air bladders, and a sixth set of air bladders, each set of air bladders comprising at least one of the air bladders, the air-flow subsystem comprising further comprising:
   a first transfer pump operably coupled between the first set of the air bladders and the second set of the air bladders;
   a second transfer pump operably coupled between the third set of the air bladders and the fourth set of the air bladders; and
   a third transfer pump operably coupled between the fifth set of the air bladders and the sixth set of the air bladders.

* * * * *